(12) United States Patent
Liu

(10) Patent No.: US 7,200,496 B2
(45) Date of Patent: Apr. 3, 2007

(54) METHOD OF PREDICTING WEAR OF A DIE SURFACE

(75) Inventor: Huimin Liu, Northville, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 10/908,955

(22) Filed: Jun. 2, 2005

(65) Prior Publication Data

US 2006/0276993 A1    Dec. 7, 2006

(51) Int. Cl.
*G06F 19/00*    (2006.01)
(52) U.S. Cl. .......................................... 702/35; 700/175
(58) Field of Classification Search .............. 702/166, 702/34; 700/175
See application file for complete search history.

(56) References Cited

U.S. PATENT DOCUMENTS

| | | | |
|---|---|---|---|
| 3,834,219 A | 9/1974 | Brauer | |
| 4,633,720 A | 1/1987 | Dybel et al. | |
| 5,311,759 A | 5/1994 | Mangrulkar et al. | |
| 5,423,199 A | 6/1995 | Mangrulkar | |
| 5,917,726 A * | 6/1999 | Pryor | 700/95 |
| 6,484,106 B1 | 11/2002 | Schoch | |
| 6,487,506 B1 * | 11/2002 | Schoch | 702/34 |
| 6,615,103 B2 * | 9/2003 | Fujishima et al. | 700/175 |
| 6,722,009 B2 * | 4/2004 | Kojima et al. | 29/421.1 |
| 6,738,729 B1 | 5/2004 | Schoch | |
| 6,922,640 B2 * | 7/2005 | Vezzu et al. | 702/34 |

OTHER PUBLICATIONS

Dong-Hwan Kim, Byung-Min Kim, and Chung-Kil Kang, "Die Life Estimation of Hot Forging Surface Treatment and Lubricants." International Journal of Precision Engineering and Manufacturing vol. 5, Oct. 2004.*
Rudi ter Haar, "Friction in Sheet Metal Forming, the influence of (local) contact conditions and deformation." Thesis Universiteit Twente, Enschede, thesis reference number ISBN 90-9009296-X. 1967.*
ASM Handbook Online. ASM International 2003. Including: Roger Lewis and Rob Dwyer-Joyce, "Impact Wear Modeling" Book 11, section "Wear Failures", "Impact Wear Failures". Joseph H. Tylczak, "Effect of Environment on Abrasive Wear." Book 18, section "Wear", "Abbrasive Wear".*

* cited by examiner

*Primary Examiner*—John Barlow
*Assistant Examiner*—Jonathan Moffat
(74) *Attorney, Agent, or Firm*—Raymond L. Coppiellie; Brooks Kushman P.C.

(57) ABSTRACT

A method of predicting wear of a die surface. The method calculates a wear depth value based on a set of die characteristic values, a set of sheet material characteristic values, a coefficient of friction value, and material draw-in distance.

18 Claims, 1 Drawing Sheet

METHOD OF PREDICTING WEAR OF A DIE SURFACE

BACKGROUND OF THE INVENTION

1. Field of the Invention

The present invention relates to a method of predicting wear of a die surface, and more particularly to a method of predicting wear of a draw bead surface of a stamping die.

2. Background Art

Stamping operations are used to fabricate a variety of automotive components, such as vehicle body panels. A stamping operation may utilize one or more dies to form a part having a desired shape. Die surfaces, such as draw bead surfaces, are susceptible to wear due to high localized contact pressures and friction. Wear may result in an inability to maintain dimensional tolerances, reduced part surface quality, and further degradation to the die.

Previously, part or die surfaces were inspected to detect die surface wear. These inspection techniques detected wear after it occurred, thereby increasing scrap and reducing process efficiency. Moreover, inspection techniques rely on manual observations that are inherently subjective.

Before applicant's invention, a method was needed for predicting die wear. In addition, a method was needed that proactively predicted die wear so that preventive or corrective actions could be taken to extend die life and reduce downtime. In addition, a method was needed that could predict die wear before part quality was affected, thereby reducing scrap and surface quality issues. In addition, a method was needed that was compatible with various part materials, material geometries, die surface coatings, die geometries, and lubrication conditions. Problems associated with the prior art as noted above and other problems are addressed by applicants' invention as summarized below.

SUMMARY OF THE INVENTION

According to one aspect of the present invention, a method of predicting wear of a die surface is provided. The method includes the steps of providing a radius value and a hardness value of the die surface, providing a thickness value and a yield strength of a sheet material, providing a coefficient of friction between the die surface and the sheet material, providing a material draw-in distance value, and calculating a wear depth value based on the radius, hardness, thickness, yield strength, coefficient of friction, and material draw-in distance values.

The wear depth value may be calculated with a computation device. The computation device may be a controller of a press.

A total wear depth value may be determined based on the average wear depth value and a number of die hits. The total wear depth value may be compared to a threshold value. An indicator signal may be generated when the total wear depth value exceeds the threshold value.

The die surface may be disposed proximate a draw bead. The draw bead may have a male or a female configuration.

According to another aspect of the present invention, a method of predicting wear of a surface of a draw bead of a die is provided. The method includes the steps of providing a computation device, determining a draw bead radius value, a draw bead hardness value, a material thickness value, a yield strength value, a coefficient of friction value, and a material draw-in distance value. An average wear depth value may be calculated based on the draw bead radius value, draw bead hardness value, material thickness value, yield strength value, coefficient of friction value, and material draw-in distance value.

The method may include the step of determining a number of die hits and calculating a total wear depth value based on the average wear depth value and the number of die hits.

The method may include the step of calculating a die hit value indicative of a number of die hits to attain a target level of wear. The die hit value may be based on the average wear depth value and a predetermined total wear depth value.

According to another aspect of the present invention, a method of predicting wear of a surface of a die is provided. The die is adapted to form a sheet material into a desired shape. The method includes the steps of providing a set of die characteristic values, providing a set of sheet material characteristic values, providing a coefficient of friction value and a material draw-in distance value, and calculating an average wear depth value based on the set of die characteristic values, a set of sheet material characteristic values, coefficient of friction value, and material draw-in distance value.

The set of die characteristic values may include a radius of the surface of the die, a hardness of the surface of the die, a draw bead radius value, and/or draw bead hardness value. The set of sheet material characteristic values may include a thickness value and a yield strength value.

The method may include the step of calculating a total wear depth value based on the average wear depth value and an elapsed number of hits of a press that receives the die.

DETAILED DESCRIPTION OF THE PREFERRED EMBODIMENT(S)

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for the claims and/or as a representative basis for teaching one skilled in the art to variously employ the present invention.

Figure 1:
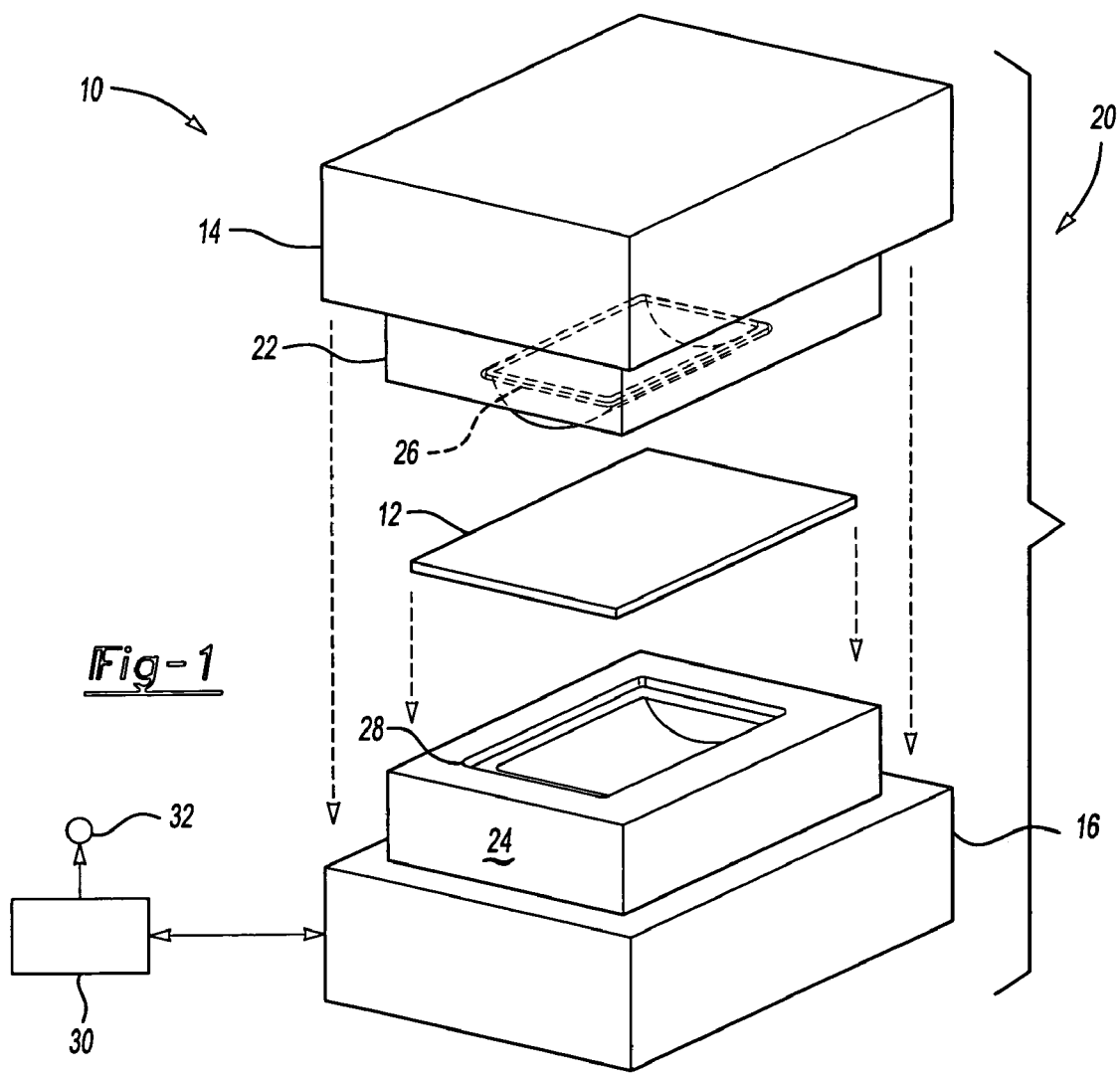
FIG. 1 is an exploded perspective view of a portion of a press having a die.

Referring to FIG. 1, a schematic representation of a press 10 is shown. The press 10 may be configured to perform a forming operation on a blank or sheet material 12, such as sheet metal, during a production cycle. For example, the press 10 may be configured to perform stamping operations, such as drawing, trimming, piercing, forming, and/or restriking.

The press 10 may have any suitable configuration and may be of any suitable type. In the embodiment shown, the press 10 includes a crown or upper die bolster 14 and a bed or lower die bolster 16. In addition, the press 10 may be a double-action press in which the upper and lower die bolsters 14,16 are moveable or a single-action press in which one bolster is moveable and the other bolster is fixed.

The press 10 may include a die set 20 having an upper die 22 and a lower die 24. The upper and lower dies 22,24 may be disposed on different sections of the press 10. In the embodiment shown, the upper die 22 is disposed on the upper die bolster 14 of the press 10 and the lower die 24 is disposed on the lower die bolster 16 of the press 10.

The upper and lower dies 22,24 may have contoured surfaces that are configured to form the sheet material 12 into a desired shape. These contoured surfaces may include one or more bead areas. In the embodiment shown, a male draw bead 26 is provided on the upper die 22 and a female draw bead 28 is provided on the lower die 24. The male and female draw beads 26,28 may have any suitable configuration. Moreover, the male draw bead 26 may be at least partially received in the female draw bead 28 during press operation.

A computation device 30 may be provided to receive input signals and generate output signals. The computation device 30 may include a controller of any suitable type, such as a microprocessor-based controller like a programmable logic controller (PLC), a non-microprocessor-based controller, such as one or more relays, or combinations thereof. The computation device 30 may communicate with one or more aspects of the press 10 or may have a stand-alone configuration. In addition, the computation device 30 may be adapted to provide a signal to an indicator 32 that provided a visual and/or audible signal.

Figure 2:
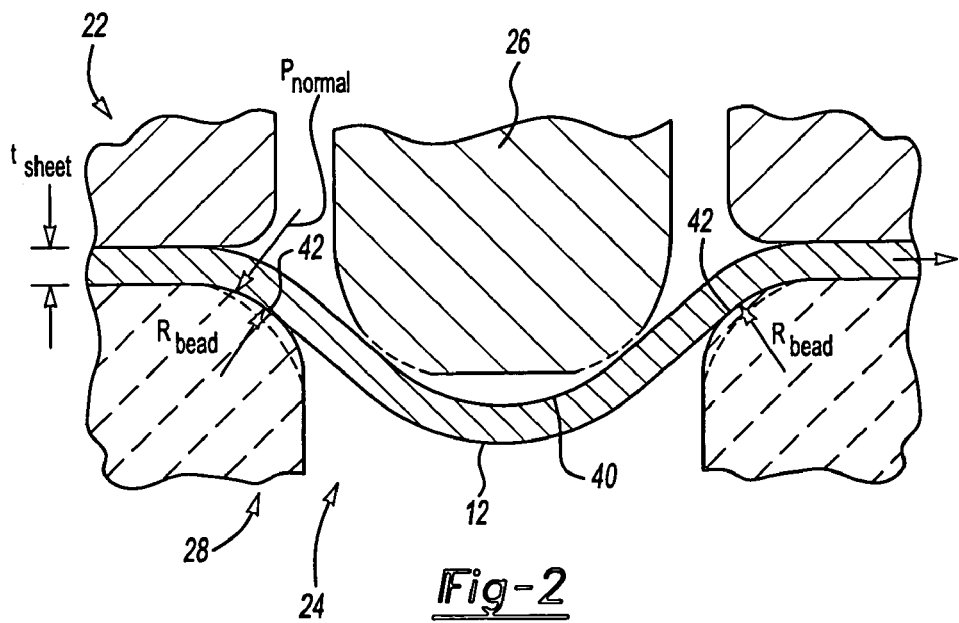
FIG. 2 is a magnified section view of a bead area of the die and sheet material being formed in the die.

Referring to FIG. 2, a magnified section view is shown of the bead area of the die set 20 during forming of the sheet material 12. Prior to forming, the sheet material 12 may have a generally planar configuration and a generally constant thickness, designated $t_{sheet}$. At least a portion of the sheet material 12 attains a different configuration during the forming process. In the embodiment shown, the sheet material 12 is held between binder portions of the upper and lower dies 22,24 proximate the bead area. At least a portion of the surface 40 of the male draw bead 26 engages the sheet material 26 and exerts pressure, designated $P_{normal}$, against the surface 42 along one or more points of contact or areas of contact. For instance, the male bead may contact the sheet material 12 at one or more localized points rather than across its entire end surface and provide high localized stresses. The points or areas of contact are subject to wear. Wear may be indicated in various ways, such as by a loss of material from a die surface or surface coating, scratches, galling, pitting, and/or dimensional changes to bead radii, which is represented by the dashed lines.

The draw bead surfaces 40,42 may have any suitable shape, such as a rectilinear, contoured, or curved shape. In the embodiment shown, each draw bead surface 40,42 has a radius, designated $R_{bead}$. At least a portion of these radii may be part of the contact area and may be used to restrain or inhibit flow of the sheet material. In addition, these areas are subject to high localized contact pressures, temperatures, and shear stresses that may result in delamination of a surface coating or draw bead surface wear.

Wear of a die surface may result in an inability to maintain dimensional tolerances, surface defects, scrap, and increased maintenance needs. Wear may occur in various forms due to various factors. These factors may be grouped into four primary categories or wear mechanisms, namely adhesive wear, abrasive wear, erosive wear, and fatigue wear.

Adhesive wear relates to the disengagement of material of one surface due to adhesion to another surface. This disengagement may occur when asperities on one surface, such as a die surface, contact asperities on another surface, such as a sheet material surface. The disengaged material, which may be in the form of particles or fragments, may remain adhered to the receiving surface, transfer back to the original surface, or form loose particles. Adhesive wear may be accelerated by the high pressures, temperatures, and friction that occur at the contact surfaces during press operation.

Abrasive wear relates to the disengagement of material of a softer surface due to contact with a harder surface, such as when a hard, rough surface slides across and scratches a surface made of a softer material. Disengaged material generally results in loose particles.

Erosive wear relates to disengagement of material that has been subject to chemical and/or electrochemical attack, such as that which may be due to interactions with the environment and/or lubricants. A chemical attack may result in the formation of a corrosive product on a die surface that may be sheared due to contact with another surface. Erosive wear may be accelerated by the high pressures and temperatures present during press operation at the contact surfaces of the die and sheet material surfaces.

Fatigue wear relates to the formation of surface anomalies, such as cracks, due to cyclic loading and unloading of a die surface. Fatigue wear may result in delamination and the disengagement of large surface fragments.

In a stamping or drawing operation, die surface wear may occur in the mixed modes of adhesive, erosive, and fatigue wear. Abrasive wear is less prevalent since die surfaces are normally harder and significantly smoother than the sheet material operated on by the die. The methodology described below focuses primarily on adhesive wear as well as consideration of erosive and fatigue wear phenomena.

The amount of adhesive wear of a die surface, such as a draw bead surface, is proportional to the friction force or shear stress at the contact area and to the material draw-in distance across the die surface by another surface, such as a sheet material surface that contacts the die. In addition, the amount of wear is inversely proportional to the hardness of the die surface.

The average wear depth over the contact area per die "hit" may be based on the expression:

$$h_{wear} = c_{wear} \times \mu \times \frac{\sigma_y^a \times t_{sheet}^b}{H_{bead} \times R_{bead}^c} \times X_{slide} \tag{1}$$

where:

$h_{wear}$ is the average wear depth of the bead surface per hit (in m), $c_{wear}$, a, b, and c are constants, μ is the coefficient of friction at the interface between the die surface and the sheet material, $\sigma_y$ is the yield strength of the sheet material (in N/m²), $t_{sheet}$ is the thickness or gage of the sheet material (in m), $R_{bead}$ is the radius of the draw bead (in m), $H_{bead}$ is the hardness of the die surface (in N/m²), and $X_{slide}$ is the draw-in distance of the sheet material (in m).

The constant $c_{wear}$ is indicative of the likelihood that an adhesive fragment would form and is affected by temperature, erosion, and fatigue.

Since $h_{wear}$ is the average wear depth of the bead surface per hit, the total wear depth over an elapsed number of die hits may be expressed by multiplying the average wear depth ($h_{wear}$) by the total number of die hits (n) to yield expression 2:

$$h_{\text{total\_wear}} = n \times c_{wear} \times \mu \times \frac{\sigma_y^a \times t_{sheet}^b}{H_{bead} \times R_{bead}^c} \times X_{slide} \quad (2)$$

where:

$h_{total\_wear}$ is the total wear depth of the contact area of the bead surface at the maximum normal contact pressure (in m), and n is the total number of die hits.

Expression 2 may be used to predict the total wear depth for known sheet material characteristics (e.g., yield strength and thickness), die characteristics (e.g, draw bead surface coating, radius), lubrication, and draw-in distance values. Moreover, expression 2 may be used in die design. For instance, a desired die surface coating thickness may be selected such the predicted total wear depth does not exceed the thickness of the coating. Also, expression 2 may be rearranged to determine a draw bead radius and draw-in distance that reduces or minimizes draw bead wear for given volume, material, lubrication, and coating properties. Expression 2 may be rewritten to provide the total number of die hits to attain a predetermined level of die surface wear:

$$n = \frac{h_{\text{total\_wear}}}{c_{wear} \times \mu \times X_{slide}} \times \frac{H_{bead} \times R_{bead}^c}{\sigma_y^a \times t_{sheet}^b} \quad (3)$$

The expressions presented above may be incorporated in a methodology for predicting wear of a bead surface. In at least one embodiment, the method includes the steps of providing input values or input signals and calculating an average wear depth value, a total wear depth value, and/or a number of die hits in the manner previously discussed. Inputs used by the method may be preprogrammed, manually entered, provided by sensors, or combinations thereof.

The present invention also contemplates rewriting expression 2 to solve for any other variable, thereby aiding in die design, surface specifications, lubricant selection or die surface treatment standards. The methodology may also be incorporated with equipment maintenance practices. For instance, the wear depth and hit calculations may be incorporated with maintenance scheduling practices, such as a preventative maintenance program.

As will be appreciated by one of ordinary skill in the art, the methodology and expressions presented above may be represented as control logic which may be implemented using hardware, software, or combination of hardware and software. For example, the various functions may be performed using a programmed microprocessor. The control logic may be implemented using any of a number of known programming or processing techniques or strategies and may not be limited to a particular sequence.

This invention is independent of the particular programming language, operating system processor, or circuitry used to develop and/or implement the control logic illustrated. Likewise, depending upon the particular programming language and processing strategy, various functions may be performed in the sequence illustrated at substantially the same time or in a different sequence while accomplishing the features and advantages of the present invention. The illustrated functions may be modified or in some cases omitted without departing from the spirit or scope of the present invention.

While the best mode for carrying out the invention has been described in detail, those familiar with the art to which this invention relates will recognize various alternative designs and embodiments for practicing the invention as defined by the following claims.

What is claimed is:

1. A method of predicting wear of a die surface, the method comprising:

providing a radius value and a hardness value of the die surface;

providing a thickness value and a yield strength of a sheet material;

providing a coefficient of friction between the die surface and the sheet material;

providing a material draw-in distance value;

calculating a wear depth value in accordance with the following equation:

$$h_{wear} = C_{wear} \times \mu \times \frac{\sigma_y^a \times t_{sheet}^b}{H_{bead} \times R_{bead}^c} \times X_{slide}$$

where:

$h_{wear}$ is the average wear depth of the bead surface per hit, $C_{wear}$, a, b, and c are constants.

$\mu$ is the coefficient of friction at the interface between the die surface and the sheet material.

$\sigma_y$ is the yield strength of the sheet material, $t_{sheet}$ is the thickness of the sheet material, $R_{bead}$ is the radius of the draw bead, $H_{bead}$ is the hardness of the die surface, and $X_{slide}$ is the draw-in distance of the sheet material;

generating a signal based on the wear depth value; and transmitting the signal to a computation device.

2. The method of claim 1 wherein the die surface is disposed proximate a draw bead.

3. The method of claim 2 wherein the draw bead has a male configuration.

4. The method of claim 2 wherein the draw bead has a female configuration.

5. The method of claim 1 further comprising providing a computation device for calculating the wear depth value.

6. The method of claim 5 wherein the computation device is a controller associated with a press.

7. The method of claim 1 further comprising the step of comparing the wear depth value to a threshold value and generating an indicator signal when the wear depth value exceeds the threshold value.

8. A method of predicting wear of a surface of a draw bead of a die, the method comprising:

providing a computation device;

determining a draw bead radius value and a draw bead hardness value;

determining a material thickness value and a yield strength of a sheet material operated on by the die;

determining a coefficient of friction between the surface of the draw bead and the sheet material;

determining a material draw-in distance value;

calculating an average wear depth value in accordance with the following equation:

$$h_{wear} = C_{wear} \times \mu \times \frac{\sigma_y^a \times t_{sheet}^b}{H_{bead} \times R_{bead}^c} \times X_{slide}$$

where:

$h_{wear}$ is the average wear depth of the bead surface per hit, $C_{wear}$, a, b, and c are constants, μ is the coefficient of friction at the interface between the draw bead surface and the sheet material, $\sigma_y$ is the yield strength of the sheet material, $t_{sheet}$ is the thickness of the sheet material, $R_{bead}$ is the radius of the draw bead, $H_{bead}$ is the hardness of the draw bead, and $X_{slide}$ is the draw-in distance of the sheet material;

generating a signal based on the wear depth value; and transmitting the signal to a computation device.

9. The method of claim 8 wherein the draw bead has a male configuration.

10. The method of claim 8 wherein the draw bead has a female configuration.

11. The method of claim 8 further comprising determining a number of die hits and calculating a total wear depth value based on the average wear depth value and the number of die hits.

12. The method of claim 8 further comprising the step of calculating a die hit value indicative of a number of die hits to attain a target level of wear based on the average wear depth value and a predetermined total wear depth value.

13. The method of claim 12 wherein the computation device is associated with a press that receives the die and the method further comprises the step of providing an indicator signal when an elapsed number of die hits exceeds the die hit value.

14. A method of predicting wear of a surface of a die, the die being adapted to form a sheet material into a desired shape, the method comprising:

providing a set of die characteristic values;

providing a set of sheet material characteristic values;

providing a coefficient of friction value and a material draw-in distance value associated with movement of the sheet material across the surface of the die;

calculating an average wear depth value in accordance with the following equation:

$$h_{wear} = C_{wear} \times \mu \times \frac{\sigma_y^a \times t_{sheet}^b}{H_{bead} \times R_{bead}^c} \times X_{slide}$$

where:

$h_{wear}$ is the average wear depth of the bead surface per hit, $C_{wear}$, a, b, and c are constants, μ is the coefficient of friction at the interface between the die surface and the sheet material, $\sigma_y$ is the yield strength of the sheet material, $t_{sheet}$ is the thickness of the sheet material, $R_{bead}$ is the radius of the draw bead, $H_{bead}$ is the hardness of the die surface, and $X_{slide}$ is the draw-in distance of the sheet material;

generating a signal based on the wear depth value; and transmitting the signal to a computation device.

15. The method of claim 14 wherein the set of die characteristic values includes a radius of the surface of the die and a hardness of the surface of the die.

16. The method of claim 14 wherein the set of die characteristic values includes a draw bead radius value and a draw bead hardness value.

17. The method of claim 14 wherein the set of sheet material characteristic values includes a thickness value and a yield strength value.

18. The method of claim 14 further comprising calculating a total wear depth value based on the average wear depth value and an elapsed number of hits of a press that receives the die.

* * * * *